United States Patent [19]

Trofast

[11] Patent Number: 6,030,604
[45] Date of Patent: *Feb. 29, 2000

[54] FORMULATION FOR INHALATION

[75] Inventor: Jan Trofast, Lund, Sweden

[73] Assignee: Astra Aktiebolag, Sweden

[*] Notice: This patent is subject to a terminal disclaimer.

[21] Appl. No.: 09/004,902

[22] Filed: Jan. 9, 1998

Related U.S. Application Data

[63] Continuation-in-part of application No. 08/316,938, Oct. 3, 1994.

[30] Foreign Application Priority Data

Jan. 20, 1997 [SE] Sweden ................................. 9700135

[51] Int. Cl.$^7$ ............................ A61K 9/14; A61K 31/56; A61K 31/58; A61K 31/135
[52] U.S. Cl. ............................ 424/46; 514/171; 514/174; 514/653; 514/826
[58] Field of Search ................................. 514/171, 174, 514/653, 826; 424/46

[56] References Cited

U.S. PATENT DOCUMENTS

| | | | |
|---|---|---|---|
| 4,199,578 | 4/1980 | Stevenson | 424/240 |
| 4,414,209 | 11/1983 | Cook et al. | 424/243 |
| 4,524,769 | 6/1985 | Wetterlin | 128/203.15 |
| 4,534,345 | 8/1985 | Wetterlin | 128/203.15 |
| 4,590,206 | 5/1986 | Forrester et al. | 514/456 |
| 5,192,548 | 3/1993 | Velasquez et al. | 424/443 |
| 5,355,872 | 10/1994 | Riggs et al. | 128/200.21 |
| 5,474,759 | 12/1995 | Fassberg et al. | 424/45 |
| 5,503,869 | 4/1996 | Van Oort | 427/2.14 |
| 5,538,999 | 7/1996 | Clark et al. | 514/653 |
| 5,551,489 | 9/1996 | Trofast et al. | 141/18 |
| 5,562,923 | 10/1996 | Trofast et al. | 424/489 |
| 5,614,514 | 3/1997 | Axelsson et al. | 514/174 |
| 5,628,307 | 5/1997 | Clark et al. | 128/203.15 |
| 5,637,620 | 6/1997 | Trofast et al. | 514/630 |
| 5,647,347 | 7/1997 | Van Oort | 128/203.15 |
| 5,654,007 | 8/1997 | Johnson et al. | 424/489 |
| 5,655,523 | 8/1997 | Hodson et al. | 128/315 |
| 5,674,860 | 10/1997 | Carling et al. | 514/171 |
| 5,674,861 | 10/1997 | Andersson et al. | 514/174 |
| 5,700,410 | 12/1997 | Nakamichi et al. | 264/122 |
| 5,709,884 | 1/1998 | Trofast | 424/489 |
| 5,736,124 | 4/1998 | Akehurst et al. | 424/45 |

FOREIGN PATENT DOCUMENTS

| | | |
|---|---|---|
| 9311773 | 6/1993 | WIPO . |
| 9505805 | 3/1995 | WIPO . |
| WO 95/09616 | 4/1995 | WIPO . |
| WO 98/15280 | 4/1998 | WIPO . |

*Primary Examiner*—Kevin E. Weddington
*Attorney, Agent, or Firm*—Fish & Richardson P.C.

[57] ABSTRACT

A dry powder composition comprising one or more potent pharmaceutically active substances and a carrier substance, all of which are in finely divided form, wherein the formulation has a poured bulk density of from 0.28 to 0.38 g/ml is useful in the treatment of respiratory disorders.

34 Claims, No Drawings

FORMULATION FOR INHALATION

This is a continuation-in-part of U.S. application Ser. No. 08/316,938, filed Oct. 3, 1994 (pending).

FIELD OF THE INVENTION

The present invention provides a new pharmaceutical formulation, its preparation and its use.

BACKGROUND TO THE INVENTION

Potent drugs for administration by inhalation are generally formulated in association with carriers such as lactose because of the problem of preparing accurate doses. When such drugs are diluted, variations in the weight of the formulation result in a smaller drug dosage variation rate compared with when they are not diluted. These formulations have generally consisted of coarse particles of the carrier with fine particles of the drug, which combination is generally known as an ordered mixture.

The invention provides an improved formulation which, in systems designed to imitate inhalation has been found to give an improved dispersion of the drug.

DESCRIPTION OF THE INVENTION

According to the invention there is provided a dry powder composition comprising one or more potent pharmaceutically active substances and a carrier substance, all of which are in finely divided form, wherein the formulation has a poured bulk density of from 0.28 to 0.38 g/ml, preferably from 0.30 to 0.36 g/ml.

The poured bulk density according to the present invention is measured using known techniques, for example those described in "Powder testing guide: Methods of measuring the physical properties of Bulk powders" L. Svarovsky, Elsevier Applied Science 1987, pp 84–86.

A potent pharmaceutically active substance suitable for use in the invention is, for example, an antiarrhythmic drug, tranquilizer, cardiac glycoside, hormone, hypertensive drug, antidiabetic or anticancer drug, sedative or analgesic drug, antibiotic, antirheumatic drug, immunotherapy, antifungal or antihypotension drug, vaccine, antiviral drug, protein (e.g. insulin), peptide, vitamin, or a cell surface receptor blocker. It is preferably a glucocorticosteroid, particularly one which is metabolized rapidly, for example beclomethasone dipropionate (BDP), beclomethasone monopropionate (BMP), flunisolide, triamcinolone acetonide, fluticasone propionate, ciclesonide, budesonide, rofleponide or derivatives thereof, momethasone, tipredane, RPR 106541 and/or a β2-agonist such as terbutaline, salbutamol, formoterol, salmeterol, TA 2005, pircumarol or a pharmaceutically acceptable salt thereof; and/or a prophylactic agent such as sodium chromoglycate or nedocromil sodium.

Suitable physiologically acceptable salts include acid addition salts derived from inorganic and organic acids, for example the chloride, bromide, sulphate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof The carrier substance is preferably a mono-, di- or polysaccharide, a sugar alcohol or another polyol. Suitable carriers are, for example, lactose, glucose, raffinose, melezitose, lactitol, maltitol, trehalose, sucrose, mannitol; and starch. Lactose is particularly preferred, especially in the form of its monohydrate.

The ingredients of the formulation according to the invention must both be in a finely divided form, i.e. their mass median diameter should generally be less than 10 μm, preferably from 1 to 7 μm, as measured by a laser diffraction instrument or a coulter counter. The ingredients may be produced in the desired particle size using methods known to those of skill in the art, e.g. milling, micronization or direct precipitation.

The combination of budesonide and formoterol is particularly preferred. Formoterol is preferably used in the form of its fumarate, especially the dihydrate.

When the one or more potent pharmaceutically active substances used in the invention are formoterol and budesonide, the molar ratio of formoterol to budesonide in the composition of the invention is preferably from 1:2500 to 12:1, more preferably from 1:555 to 2:1, most preferably from 1:133 to 1:6. The composition according to the invention is preferably formulated to provide a daily dose of formoterol of from 2 to 120 nmol (more preferably from 7 to 70 nmol). When formoterol is used in the form of formoterol fumarate dihydrate, the composition is preferably formulated to provide a daily dose of formoterol fumarate dihydrate of from 1 to 50 μg, more preferably from 3 to 30 μg. The composition according to the invention is preferably formulated to provide a daily dose of budesonide of from 45 to 2200 μg, more preferably from 65 to 1700 μg.

More preferably the composition of the invention comprises, as a unit dose, 6 μg of formoterol fumarate dihydrate and 100 μg of budesonide, or 4.5 μg of formoterol fumarate dihydrate and 80 μg of budesonide, either of which can be administered up to four times a day. Alternatively the composition of the invention comprises, as a unit dose, 12 μg of formoterol fumarate dihydrate and 200 μg of budesonide, or 9 μg of formoterol fumarate dihydrate and 160 μg of budesonide, either of which is administered once or twice a day.

Most preferably the composition used in the invention comprises, as a unit dose, 6 μg of formoterol fumarate dihydrate and 200 μg of budesonide, or 4.5 μg of formoterol fumarate dihydrate and 160 μg of budesonide, either of which is administered up to four times a day. Alternatively the composition of the invention comprises, as a unit dose, 12 μg of formoterol fumarate dihydrate and 400 μg of budesonide, or 9 μg of formoterol fumarate dihydrate and 320 μg of budesonide, either of which is administered once or twice a day.

According to the invention there is further provided a process for preparing a composition according to the invention which comprises (a) micronizing the one or more potent pharmaceutically active substances and the carrier substance;

(b) optionally conditioning the product; and (c) spheronizing until the desired bulk density is obtained.

The process preferably further comprises a low energy remicronization step after step (b).

The formulation according to the invention may be made by conventional techniques known per se. Such production processes generally comprise micronizing the ingredients to the required size, removing any amorphous areas on the particles obtained by, for example, the methods described in WO 92/18110 or WO 95/05805 and then agglomerating, spheronizing and sieving the powder obtained. The size of the agglomerates obtained is preferably in the range of from 100 to 2000 μm, more preferably from 100 to 800 μm. The bulk density of the formulation produced may be adjusted by varying the components and the process empirically, for example the bulk density can be increased by lengthening the time in which the particles are tumbled in a spheronizing device.

In solid-solid mixing, one of the most important features is to ensure content uniformity. The major problem encountered in the powder mixing of fine powders is the inability of mixers to break down powder agglomerates. It has been found that a remicronization step after the conditioning step of the fine powder with low energy input is advantageous. It should generally be carried out using enough energy to break down powder agglomerates but not with so much energy that the size of the particles themselves is affected. Such a step gives a composition wherein the active substance and carrier substance are substantially uniformly distributed, having for example a relative standard deviation of less than 3% (preferably less than 1%) and does not disturb the crystallinity of the fine particles.

The formulation according to the invention may be administered using any known dry powder inhaler, for example the inhaler may be a single or a multi dose inhaler, and may be a breath actuated dry powder inhaler, for example Turbuhaler (trade mark). The invention further provides use of a composition according to the invention in the manufacture of a medicament for use in therapy. The composition according to the invention is useful in the treatment of respiratory disorders, particularly asthma. The invention also provides a method of treating a patient suffering from a respiratory disorder which comprises administering to the patient a therapeutically effective amount of a composition according to the invention.

The invention is illustrated, but not limited, by reference to the following Examples.

EXAMPLE 1

0.0315 Parts of formoterol fumarate dihydrate and 2.969 parts of lactose monohydrate are mixed in a tumbling mixer (Turbula) to an evenly distributed mixture, whereafter the mixture is micronised in a spiral jet mill using a pressure and feeding rate suitable to obtain a particle size of less than 3 $\mu$m (mass median diameter as measured by a coulter counter). The micronised particles were then treated using the method disclosed in WO 95/05805 to remove amorphous regions in their crystal structure. The powder was then agglomerated by feeding the powder into a twin screw feeder (K-Tron), sieving in an oscillating sieve (0.5 mm mesh size), spheronising in a rotating pan with a peripheral speed of 0.5 m/s for 4 minutes and then sieving again using the same sieve, then spheronising once more for 6 minutes before final sieving (mesh size 1.0 mm) giving a powder with a bulk density of 0.32 g/ml.

EXAMPLE 2

Example 1 was repeated but the powder was remicronised in a spiral jet mill at a lower pressure (about 1 bar) after micronisation and conditioning such that the step of treating the particles in the manner described in WO 95/05805 was not required giving a powder with a bulk density of 0.32 g/ml.

EXAMPLE 3

9 Parts of budesonide and 91 parts of lactose monohydrate were micronized separately in a spiral jet mill at a pressure of about 6–7 bars to give a particle size of less than 3 $\mu$m before being mixed thoroughly in a Turbula mixer. Before mixing, the lactose monohydrate powder was conditioned according to the method described in WO 95/05805. The mixture was remicronized in a spiral jet mill at a pressure of only about 1 bar to obtain a uniform mixture. The powder was then agglomerated and spheronized as described in Example 1 to obtain a bulk density of 0.35 g/ml.

EXAMPLE 4

60 Parts of terbutaline sulphate were micronized to a mass medium diameter of less than 2 $\mu$m in a Alpin mill 100AFG and thereafter conditioned according to the method described in U.S. Pat. No. 5,562,923. 40 Parts of lactose monohydrate were micronized (Alpin mill 100AFG) down to a mass medium diameter of less than 3 $\mu$m and thereafter conditioned according to the method described in WO 95/05805. The micronized and conditioned terbutaline sulphate and lactose monohydrate were mixed thoroughly in a Turbula mixer. The mixture was remicronized in a spiral jet mill at a pressure of only about 1 bar to obtain an evenly distributed mixture. The powder was then agglomerated and spheronized as described in Example 1 to obtain a bulk density of 0.28 g/ml.

EXAMPLE 5

Example 4 was repeated with 30 parts of terbutaline sulphate and 70 parts of lactose monohydrate to give a powder with a bulk density of 0.31 g/ml.

EXAMPLE 6

5.2 Parts of formoterol fumarate dihydrate and 896.8 parts of lactose monohydrate were mixed in a tumbling mixer to an evenly distributed mixture, whereafter the mixture was micronized in a spiral mill using a pressure and feeding rate suitable to obtain a particle size of less than 3 $\mu$m (mass medium diameter as measured by a coulter counter). The micronized particles were then treated using the method described in WO 95/05805 to remove amorphous regions in their crystal structure. 98 parts of micronized budesonide were added and the mixture was remicronized at a lower pressure in a spiral jet mill to a homogenous mixture. The powder was then agglomerated by feeding into a screw feeder (K-Tron), sieved in an oscillating sieve (0.5 mm mesh size), spheronized in a rotating pan with a speed of 23 rpm for 10 minutes, then sieved again (0.5 mm mesh size), spheronized once more before being finally sieved (0.8 mm mesh size) to give a powder with a bulk density of 0.34 g/ml.

EXAMPLE 7

Example 6 was repeated with identical conditions but using 5.2 parts of micronized formoterol fumarate dihydrate, 798.8 parts of micronized lactose monohydrate and 196 parts of micronized budesonide. The bulk density obtained was 0.34 g/ml.

I claim:

1. A dry powder composition comprising (a) two or more potent therapeutically active substances selected from the group consisting of glucocorticosteroids, β2-agonists and prophylactic agents, and (b) a carrier substance, all of which are in finely divided form, wherein the composition has a poured bulk density of from 0.28 to 0.38 g/ml.

2. A composition according to claim 1 wherein the two or more potent therapeutically active substances are (i) budesonide and (ii) formoterol or a pharmaceutically acceptable salt of formoterol.

3. A composition according to claim 1 wherein the bulk density is from 0.30 to 0.36 g/ml.

4. A composition according to claim 1 wherein the active substance and carrier substance are substantially uniformly distributed.

5. A composition according to claim 1 for use in the treatment of a respiratory disorder.

6. A process for preparing a composition according to claim 1 which comprises
   (a) micronizing the two or more potent therapeutically active substances and the carrier substance;
   (b) either before, during, or after step (a), mixing the two or more potent therapeutically active substances and the carrier substance until a substantially uniformly distributed mixture is obtained; and
   (c) spheronizing said substantially uniformly distributed mixture until a desired bulk density is obtained.

7. A process according to claim 6 which comprises a low energy remicronization step after step (c).

8. A method of making a dry powder medicament composition for use in therapy comprising providing two or more potent therapeutically active substances and a carrier substance, all of which are in finely divided form; mixing the therapeutically active substances and the carrier to form a substantially uniform mixture; and processing the mixture to obtain a poured bulk density of from 0.28 to 0.38 g/ml.

9. A method of treating a patient suffering from a respiratory disorder which comprises administering to the patient a therapeutically effective amount of a composition according to claim 1.

10. A process for preparing a composition according to claim 1 which comprises
    (a) micronizing the two or more potent therapeutically active substances and the carrier substance; and
    (b) spheronizing the micronized substances until the desired bulk density is obtained.

11. A process for preparing a composition according to claim 6, wherein said mixing step comprises combining said micronized substances in a mixer to form a first mixture, and then remicronizing said first mixture to form said substantially uniformly distributed mixture.

12. The process of claim 11 wherein said remicronizing is conducted at a pressure of about 1 bar.

13. A method of treating a patient comprising administering to the patient the dry powder composition of claim 1.

14. A method according to claim 13, wherein the two or more potent therapeutically active substances include at least one glucocorticosteroid and at least one $\beta$2-agonist.

15. A method according to claim 14, wherein the glucocorticosteroid is selected from the group consisting of beclomethasone dipropionate (BDP), beclomethasone monopropionate (BMP), flunisolide, triamcinolone acetonide, fluticasone propionate, ciclesonide, mometasone, tipredane, RPR 106541, budesonide, rofleponide and derivatives thereof.

16. A method according to claim 14, wherein the $\beta$2-agonist is selected from the group consisting of terbutaline, salbutamol, formoterol, salmeterol, TA 2005, pircumarol and pharmaceutically acceptable salts thereof.

17. A composition according to claim 2, wherein the pharmaceutically acceptable salt of formoterol is formoterol fumarate.

18. A composition of claim 17 wherein the pharmaceutically acceptable salt of formoterol is the dihydrate of formoterol fumarate.

19. A composition according to claim 1, wherein the two or more potent therapeutically active substances include at least one glucocorticosteroid and at least one $\beta$2-agonist.

20. A composition according to claim 1, wherein the glucocorticosteroid is selected from the group consisting of beclomethasone dipropionate (BDP), beclomethasone monopropionate (BMP), flunisolide, triamcinolone acetonide, fluticasone propionate, ciclesonide, mometasone, tipredane, RPR 106541, budesonide, rofleponide and derivatives thereof.

21. A composition according to claim 1, wherein the $\beta$2-agonist is selected from the group consisting of terbutaline, salbutamol, formoterol, salmeterol, TA 2005, pircumarol and pharmaceutically acceptable salts thereof.

22. A composition according to claim 19, wherein the glucocorticosteroid is selected from the group consisting of beclomethasone dipropionate (BDP), beclomethasone monopropionate (BMP), flunisolide, triamcinolone acetonide, fluticasone propionate, ciclesonide, mometasone, tipredane, RPR 106541, budesonide, rofleponide and derivatives thereof.

23. A composition according to claim 19, wherein the $\beta$2-agonist is selected from the group consisting of terbutaline, salbutamol, formoterol, salmeterol, TA 2005, pircumarol and pharmaceutically acceptable salts thereof.

24. A composition according to claim 19, wherein the two or more potent therapeutically active substances include budesonide and formoterol or a pharmaceutically acceptable salt thereof.

25. A composition according to claim 24, wherein the pharmaceutically acceptable salt of formoterol is formoterol fumarate.

26. A composition according to claim 25 wherein the pharmaceutically acceptable salt of formoterol is the dihydrate of formoterol fumarate.

27. A composition according to claim 1, wherein the prophylactic agent is selected from the group consisting of sodium chromoglycate and nedocromil sodium.

28. A composition according to claim 1, wherein the carrier substance is selected from the group consisting of monosaccharides, disaccharides, polysaccharides and polyols.

29. A composition according to claim 28, wherein the disaccharide is lactose.

30. A composition according to claim 29 wherein the disaccharide is lactose monohydrate.

31. A composition according to claim 1, wherein all of the therapeutically active substances and the carrier substance have a mass median diameter of less than 10 $\mu$m.

32. A composition according to claim 31, wherein said mass median diameter is from 1 to 7 $\mu$m.

33. A process according to claim 6, further comprising conditioning the micronized substances.

34. A process according to claim 6 wherein wherein conditioning is performed before spheronization.

* * * * *

UNITED STATES PATENT AND TRADEMARK OFFICE
CERTIFICATE OF CORRECTION

PATENT NO. : 6,030,604  
DATED : February 29, 2000  
INVENTOR(S) : Jan Trofast

It is certified that error appears in the above-identified patent and that said Letters Patent is hereby corrected as shown below:

<u>Column 1,</u>
Lines 3 and 4, please delete "This is a continuation-in-part of U.S. application Ser. No. 08/316,938, filed Oct. 3, 1994 (pending)."

Signed and Sealed this

Thirteenth Day of November, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,030,604 | Page 1 of 1 |
| APPLICATION NO. | : 09/004902 | |
| DATED | : February 29, 2000 | |
| INVENTOR(S) | : Jan Trofast | |

It is certified that error appears in the above-identified patent and that said Letters Patent is hereby corrected as shown below:

Title page, Item [63] Related U.S. Application Data, delete "Continuation-in-part of application No. 08/316,938, Oct. 3, 1994."

Title page, Item [30] Foreign Application Priority Data, delete "9700135" and insert -- 9700135-8 --.

Signed and Sealed this
Twenty-sixth Day of November, 2013

Margaret A. Focarino
*Commissioner for Patents of the United States Patent and Trademark Office*